United States Patent [19]

Okita

[11] 4,193,138
[45] Mar. 18, 1980

[54] COMPOSITE STRUCTURE VASCULAR PROSTHESES

[75] Inventor: Koichi Okita, Osaka, Japan

[73] Assignee: Sumitomo Electric Industries, Ltd., Osaka, Japan

[21] Appl. No.: 825,513

[22] Filed: Aug. 17, 1977

[30] Foreign Application Priority Data

Aug. 20, 1976 [JP] Japan .................................. 51-99808
Jul. 1, 1977 [JP] Japan .................................. 52-79387

[51] Int. Cl.² ............................................. A61F 1/24
[52] U.S. Cl. ........................................... 3/1.4; 427/2
[58] Field of Search .................... 3/1, 1.4; 128/334 R; 427/2

[56] References Cited

U.S. PATENT DOCUMENTS 3,094,762 6/1963 Jeckel ..................................... 3/1 X
3,511,684 5/1970 Huffaker ............................. 3/1.4 X

FOREIGN PATENT DOCUMENTS 2508570 10/1975 Fed. Rep. of Germany .............. 3/1.4

OTHER PUBLICATIONS

Campbell et al., "Expanded Polytetrafluoro-Ethylene as a Small Artery Substitute"; vol. XX, Trans. Amer. Soc. Artif. Int. Organs, 1974, pp. 86–90.

Primary Examiner—Clifford D. Crowder
Attorney, Agent, or Firm—Sughrue, Rothwell, Mion, Zinn and Macpeak

[57] ABSTRACT

A composite structure vascular prosthesis comprising a porous polytetrafluoroethylene tube in which the pores of the porous polytetrafluoroethylene tube are filled with at least one water-insolubilized water-soluble polymer, and a process for producing the composite structure vascular prosthesis.

28 Claims, 6 Drawing Figures

COMPOSITE STRUCTURE VASCULAR PROSTHESES

BACKGROUND OF THE INVENTION

1. Field of the Invention

This invention relates to vascular prostheses of polytetrafluoroethylene and a water-insolubilized water-soluble polymer.

2. Description of the Prior Art

Vascular prostheses made of a knitted or woven fabric of a polyester (e.g., Dacron, trade name produced by E. I. du Pont de Nemours & Co. Inc.) or polytetrafluoroethylene are currently utilized and those having a relatively large inside diameter are practical and have been used with a high degree of success. In the case of arterial vascular prostheses, the results are excellent if their inside diameter is greater than about 7 mm. However, few vascular prostheses of fine diameters are clinically acceptable. Particularly, in venous applications, the degree of success is lower than in arterial applications. The blood flow in veins is slower than in arteries, and in veins, the inhibition of platelet adhesion is especially important to prevent thrombosis. Vascular prostheses in current use do not fully meet this requirement.

It is known that some polytetrafluoroethylene tubes produced by stretching or expansion can be clinically used as vascular prostheses in arteries and veins [e.g., as disclosed in Soyer et al., "A New Venous Prosthesis," *Surgery*, Vol. 72, p. 864 (1972); Volder et al., "A-V Shunts Created in New Ways," *Trans. Amer. Soc. Artif. Int. Organs*, Vol. 19, p. 38 (1973); Matsumoto et al., "A New Vascular Prosthesis for a Small Caliber Artery," *Surgery*, Vol. 74, p. 519, (1973), and "Application of Expanded Polytetrafluoroethylene to Artificial Vessels," *Artificial Organs*, Vol. 1, p. 44 (1972), ibid., Vol. 2, p. 262 (1973) and ibid., Vol. 3, p. 337 (1974); Fujiwara et al., "Use of Goretex Grafts for Replacement of the Superior and Inferior Venae Cavae," *The Journal of Thoracic and Cardiovascular Surgery*, Vol. 67, p. 774, (1974); and Belgian Pat. No. 517,415].

The results of these clinical tests are summarized below.

When a suitable prosthesis is implanted as a conduit within the arterial system, the fine pores of the vessel are clogged by clotted blood, and the inside surface of the vessel is covered by a layer of the clotted blood. The clotted blood layer is made of fibrin, and the thickness of the layer varies according, for example, to the material and surface structure of the blood vessel. When a knitted or woven fabric or a polyester such as Dacron or polytetrafluoroethylene is used, the fibrin thickness approaches about 0.5 to about 1 mm. Accordingly, such a prosthesis is successful only with blood vessels having a caliber such that occlusion due to a thickening of the fibrin layer does not occur, namely with arteries having a inside diameter of 5 to 6 mm or more. Generally, vascular prostheses made of woven or knitted fabrics are not successful when the inside diameter is small.

On the other hand, polytetrafluoroethylene tubes which have been stretched have a micro-structure of very fine fibers and nodes connected to one another by the fibers. The diameter of the fibers, which varies according to the stretching conditions, can be made far smaller than the diameters of the fibers for the woven or knitted fabrics described above.

This structure of fibers and nodes can be described in terms of pore size, porosity, fiber length and nodular size. It has been clinically confirmed that with polytetrafluoroethylene tubes defined by a pore size of about $2\mu$ to about $30\mu$ (pore sizes of less than about $2\mu$ are not preferred), a porosity of about 78% to about 92%, a fiber length of not more than about $34\mu$ (fiber lengths of about 40 to about $110\mu$ are not preferred), a nodular size of not more than $20\mu$, and a wall thickness of about 0.3 mm to about 1 mm, little occlusion by fibrin deposition occurs, and a high patency rate is exhibited.

It was reported, however, that the patency rate in venous prostheses is far lower than that in arterial prostheses. Thus, a complete vascular prosthesis for veins has not been obtained. It was also reported that when the porosity of such a prosthesis is too high, the suture used in joining the prothesis to the vessel in a patient tends to tear the prosthesis.

In the healing process after implantation in the living body, the periphery of the polytetrafluoroethylene tube first organizes by being enveloped in connective tissue, and the inside fibrin layer organizes after the periphery. At this time, the intimas at both ends of the host's vessel extend to the inside surface of the vascular prosthesis, and the fibrin layer is replaced by the fibrous tissue which has come from the periphery of the prosthesis through the fine pores. After a certain period of time, the neo-intima in the inside surface is firmly connected to the connective tissue at the periphery thereby to complete the formation of an artery. It is known that this period is generally 4 to 6 months. It is also known that in the case of a vascular prosthesis implanted in a vein, the speed of entry of the connective tissue from the periphery is slower than in the case of arteries.

The expected mechanism of a feasible vascular prosthesis of a polytetrafluoroethylene tube is that the porous polytetrafluoroethylene tube adsorbs plasma protein, platelets adhere to the protein to form fibrin fibers which capture blood corpuscles and become a fibrin-deposited layer, and then the deposited layer forms a pseudo-intima of the vascular prosthesis. However, the thickness of the fibrin-deposited layer frequently becomes too large, and nutrient supply to the pseudo-intima or neo-intima becomes insufficient. This results in a calcification of the prosthesis wall or the occlusion of the inner cavity of the prosthesis.

SUMMARY OF THE INVENTION

Accordingly this invention provides a vascular prosthesis having a composite structure of a porous polytetrafluoroethylene tube and a water-soluble polymer provided in the pores of the porous polytetrafluoroethylene tube, the water-soluble polymer having been treated to render the polymer water-insoluble.

DETAILED DESCRIPTION OF THE INVENTION

Figure 1:
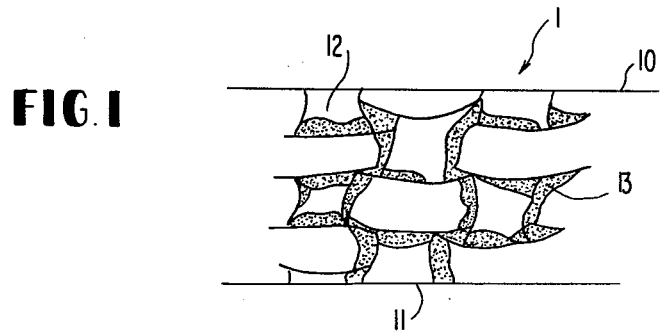
FIG. 1 is a schematic cross-section of a composite structure vascular prosthesis in accordance with the invention wherein 1 represents a porous polyethylene tube having an outer sidewall 10 and an inner sidewall 11 where pores 12 are shown filled with water-insolubilized water-soluble polymer 13. Like numerals are used in FIGS. 2–6 to represent like elements.
Figure 2:
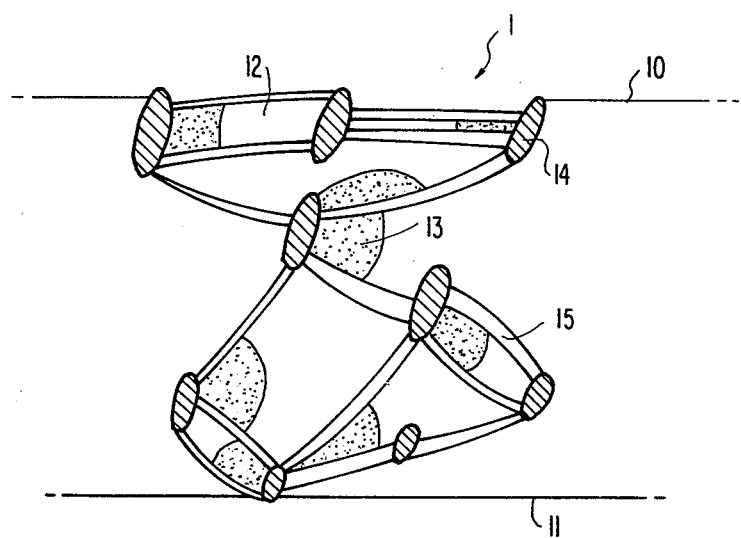
FIG. 2 is an embodiment similar to FIG. 1 except the composite structure vascular prosthesis has nodes 14 connected to one another by fibers 15, where the microstructure differs between outer sidewall 10 and inner sidewall 11.
Figure 3:
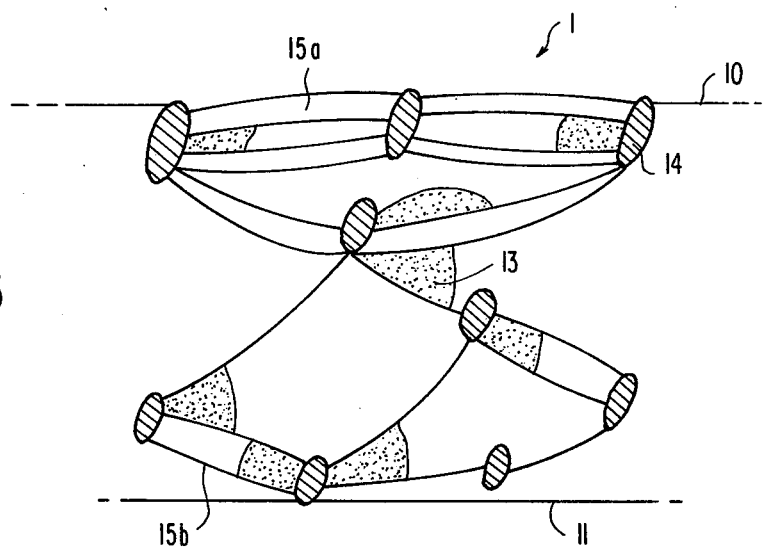
FIG. 3 is similar to FIG. 2 except that the diameter of the fibers 15a at the outer sidewall 10 is at least two times the diameter of the fibers 15b at the inner sidewall 11.
Figure 4:
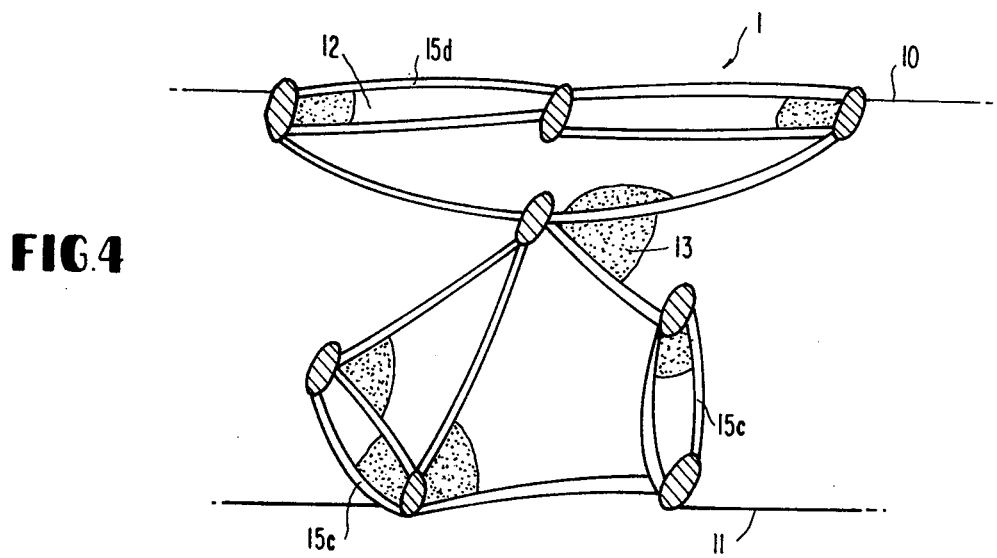
FIG. 4 is similar to FIG. 2 except that the directions of the fibers 15c at the inner sidewall 11 are distributed more radially than that of the fibers 15d at the outer sidewall 10.
Figure 5:
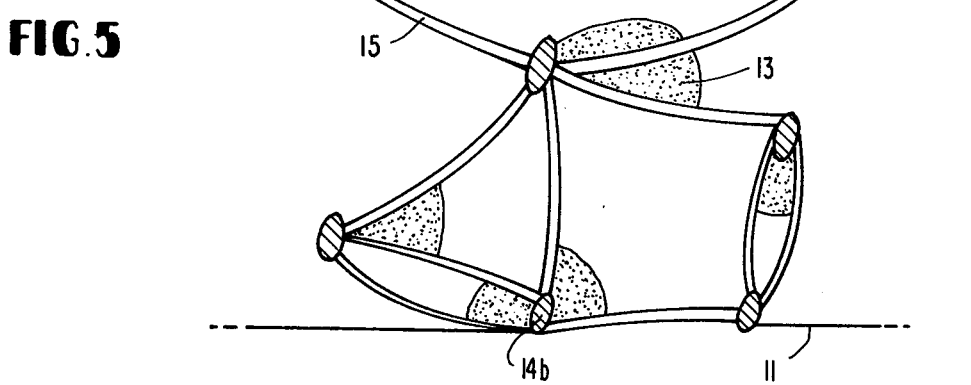
FIG. 5 is similar to FIG. 2 but the long axis of each node 14a at the outer sidewall 10 is at least two times the long axis of each node 14b at the inner sidewall 11.
Figure 6:
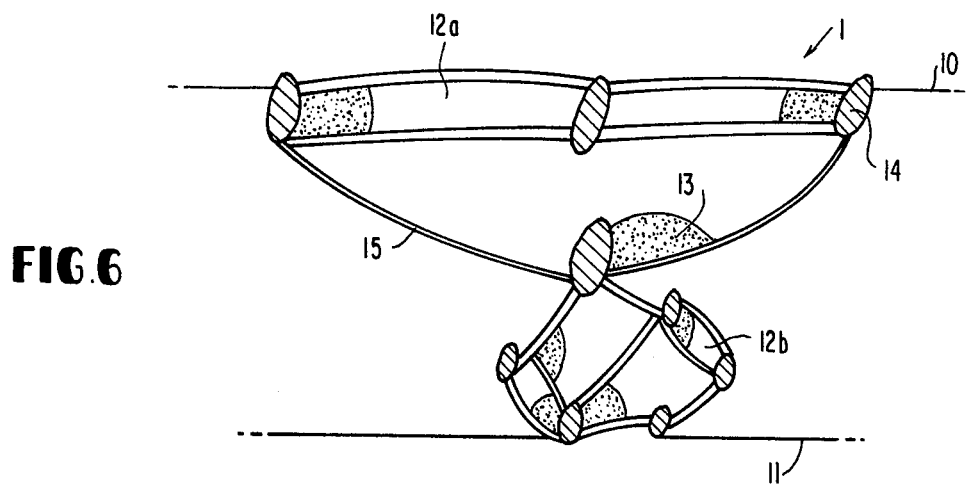
FIG. 6 is similar to FIG. 2 but the size of the pores 12a at the outer sidewall 10 is larger than the size of the pores 12b at the inner sidewall 11.

Functionally, the prosthesis of this invention can prevent thrombosis from occuring by (1) rendering the surface hydrophobic by the polytetrafluoroethylene having a low surface energy and (2) by providing the water-insolubilized water-soluble polymer in the pores of the polytetrafluoroethylene tube thereby to form a firmly bonded film of water molecules or negatively charging the polytetrafluoroethylene thereby to prevent adsorption of plasma protein which will cause fibrin deposition.

Another object of this invention is to provide a vascular prosthesis of a stretched polytetrafluoroethylene tube in which firstly, the rate of entry of the connective tissue from the periphery of the tube is increased by making the pore size of the outside surface of the tube larger than that of the inside surface; secondly, the surface stagnation of blood flow is reduced by decreasing the pore size of the inside surface of the tube; and thirdly, platelet adhesion is reduced and the amount of thrombus formation in the cavity is decreased to render the thrombus layer very thin by providing the water-insolubilized water-soluble polymer in the pores. When compared with conventional vascular prostheses having similar dimensions, with the prosthesis of the invention the neo-intima in the inside surface of the prosthesis is thin.

Still another object of this invention is to provide a vascular prosthesis in which the connective tissue from the periphery of a stretched polytetrafluoroethylene tube is making the fibrous structure at the outside surface of the tube larger than the fibrous structure at the inside surface of the tube, and consequently, nutrient is fully supplied to the neo-intima formed on the inside surface of the tube so as to prevent a calcification of the prosthesis wall by degeneration and retrogression with time, and ultimately, to increase the patency rate after implantation.

The tube is prepared by stretching a polytetrafluoroethylene tube in at least one direction and then heat-treating the stretched tube to at least about 327° C. or higher to provide a microstructure of fibers and nodes. An aqueous solution of a water-soluble polymer is filled in the pore spaces of the microstructure, and then treated to render it water-insoluble, thereby providing a composite structure. This affords a vascular prosthesis having a high patency rate, in which the neo-intima formed in the cavity of the prosthesis after implantation in a living body is made thin, and the inner cavity is not occluded.

Basically, the methods described in Japanese patent publication No. 13560/67 and U.S. Pat. No. 3,953,566 can be used to stretch and sinter a tube made of polytetrafluoroethylene. First, a liquid lubricant is mixed with an unsintered powder of polytetrafluoroethylene, and the mixture is extruded into a tubular form using a ram-type extruder. The tube is stretched in at least one direction while being heated at a temperature not higher than the sintering temperature of the tube (i.e., about 327° C.). The stretched tube is heated to a temperature of at least about 327° C. while it is fixed so that shrinkage cannot occur. This fixes the stretched and expanded structure and provides a tube having increased strength.

The water-soluble polymer, another starting material employed, is used to form a hydrophilic layer which imparts an anti-thrombosis characteristic to the polytetrafluoroethylene tube. Non-limitative examples of such a polymer are non-ionic polymers such as polyvinyl alcohol, polyethylene oxides (including polyethylene glycol), nitrogen-containing polymers such as polyacrylamide, polyvinyl pyrrolidone, polyvinylamine, and polyethyleneimine, and anionic polymers such as polyacrylic acid and polymethacrylic acid. Hydroxy esters or carboxy esters of cellulose, and polysaccharides, can sometimes be used. These polymers may be used individually or in the form of a mixture thereof, in which case both a hydrophilic layer with adsorbed water therein and a negatively charged layer can be present together. Furthermore, it is possible to produce both a polyvinyl pyrrolidone layer considered to have good affinity with the blood and a hydrophilic layer present together.

Suitable polyvinyl alcohols include complete or partial saponification products of polyvinyl acetate, and commercially available grades of polyvinyl alcohol can be utilized. Thus, the quality, such as the degree of polymerization, of the polyvinyl alcohol is uniform.

A completely saponified product of polyvinyl acetate has a degree of saponification of about 98 to 99%, and a partially saponified product thereof has a degree of saponification of about 85 to 90%. The average degree of polymerization can vary from about 300 to about 2,500.

The solubility of polyvinyl alcohol and the viscosity of the polyvinyl alcohol varies according to the degree of saponification and the degree of polymerization. Partially saponified products having a high degree of polymerization are preferred in order to cross-link them after impregnation and coating in and on a tube of polytetrafluoroethylene until they become insoluble in water.

Preferably, the concentration of the aqueous solution of polyvinyl alcohol used to treat the porous polytetrafluoroethylene tubing is about 0.01% by weight to about 12% by weight, and if the concentration is outside this range, there is scarcely any appreciable effect; or the viscosity becomes too high, and in practice, it is difficult to fill the pores of the tube with the aqueous solution of the polymer. Needless to say, the degree of saponification, the degree of polymerization, and the concentration of polyvinyl alcohol should be selected depending on the porosity, the pore size, etc. of the porous tube to be impregnated and coated with polyvinyl alcohol.

Polyethylene oxide, polyacrylamide, and polyacrylic acid are also commercially available, and commercially available materials can be used. The desired degree of polymerization can be easily chosen.

The concentration of an aqueous solution of such a water-soluble polymer can be freely selected within the range of about 0.001% by weight to about 10% by weight. However, since the viscosity of the aqueous solution of the polymer varies greatly according to the degree of polymerization, adjustment to the desired viscosity of a polymer of a high degree of polymerization must be accomplished by using a low concentration of the polymer, and adjustment to the desired viscosity of a polymer having a low degree of polymerization must be accomplished by using a high concentration of the polymer.

The viscosity of the aqueous solution of the polymer varies not only according to the concentration of the polymer therein but also according to the pH, temperature, and salt content of the aqueous solution, and the time lapse after the preparation of the aqueous solution.

When the water-soluble polymer has a relatively low degree of polymerization, it can be dissolved in an organic solvent. For example, polyacrylic acid can be dissolved in methanol, ethanol, and propanol; polyethylene oxide, in trichloroethane and dichloroethane; and polyvinyl pyrrolidone, in alcohols such as methanol and ethanol and dimethylformamide.

When the polytetrafluoroethylene tube has a small pore size, the pore spaces of the tube cannot be filled with an aqueous solution of a water-soluble polymer such as polyvinyl alcohol because the tube itself is water-repellent. First, the tube is immersed in a solvent which is soluble in water and has a surface tension of not more than about 40 dynes/cm, such as ethanol, methanol or acetone, or in an aqueous solution of a surface-active agent, and then immersed in water. The solvent diffuses into the water, and pores of the tube are filled only with water. The tube is then immersed in an aqueous solution of a water-soluble polymer. The porous tube may be immersed such that the tube is immersed completely or only one side is immersed. In order to impregnate the pores of the tube uniformly with the water-soluble polymer, the subsequent cross-linking step must be performed after a lapse of a sufficient period of time to permit diffusion of the water-soluble polymer after the immersion. If this period of time is short, the water-soluble polymer is distributed in a high concentration at the surface of the porous tube, but is present only at a low concentration in the pores of the tube. Hence, the tube is not sufficiently rendered hydrophilic. Another method for uniformly distributing the water-soluble polymer into the pores of the tube is to repeat several times the process of immersing a dilute aqueous solution of a water-soluble polymer and drying it. It was confirmed that if the porous tube impregnated with the aqueous solution is dried and again contacted with the aqueous solution, the aqueous solution more readily penetrates into the pores of the tube, and the amount of the water-soluble polymer in the pores is increased approximately two times that. The pores of the tube can also be impregnated with the aqueous solution by drawing the aqueous solution under pressure from the inner cavity of the tube.

The water-soluble polymer thus impregnated is then subjected to a cross-linking treatment to render the water-soluble polymer insoluble in water. This can be performed by techniques such as heat-treatment, a chemical reaction such as acetalization or esterification, or an ionizing radiation-induced cross-linking reaction.

Polyvinyl alcohol, polyethylene oxide, polyacrylamide, etc. are easily soluble in water, and are rendered insoluble in water by converting the polymers into a three dimensionally cross-linked network structure.

When straight-chain polyvinyl alcohol is partially crystallized by heat-treatment, one polyvinyl alcohol molecule separates into a portion included in the crystals and a portion not included in the crystals. The solubility in water of the portion included in the crystals is destroyed as if it was chemically cross-linked. The portion not included in the crystals remains amorphous, and continues to be soluble in water. However, as one molecule of polyvinyl alcohol, it is only swollen with water and is no longer soluble in the water.

When a chemical reaction such as acetalization or esterification, or an ionizing radiation-induced cross-linking reaction takes place in one molecule of a water-soluble polymer, the molecule changes from a straight-chain molecule to a cyclic molecule. If such a reaction takes place between two molecules of the water-soluble polymer, the molecules change to macrocyclic molecules. When the cross-linking reaction proceeds further and covers many molecules, the molecules change to a three-dimensional network structure. Accordingly, in order to achieve a water-insolubilization of the water-soluble polymer with less cross-linking reactions, water-soluble polymers having a higher degree of polymerization are more advantageous, and have greater swellability with water.

It is essential for water-insolubilization to induce at least two cross-linking reactions in the same molecule, and the number of cross-linking reactions needed increases as the degree of polymerization of the water-soluble polymer is decreased.

Insolubilization by heat treatment is effectively achieved with completely saponified polyvinyl alcohol. It can be accomplished by heat-treatment for about 4 to about 6 minutes at about 150° to about 160° C., and for about 1 minute at about 200° C. Preferably, at this time, the polymer is finally treated with hot water at about 90° C. or higher for at least about 5 minutes. By heat treatment, the polyvinyl alcohol intimately adheres to the matrix of the porous tube and is gelled and cross-linked. The porosity of the porous structure at this time varies slightly according to the concentration of the impregnated and coated polyvinyl alcohol, but the pore size of the structure, especially the maximum pore size or pore size distribution of the porous structure, scarcely differs from that of the matrix of the starting material.

Insolubilization by acetalization is by a chemical reaction of polyvinyl alcohol with an aldehyde by adding an aldehyde such as formaldehyde or glyoxal and a mineral acid to the aqueous solution of polyvinyl alcohol.

Insolubilization by esterification proceeds by causing a small amount of a mineral acid or an alkali to be present in a mixture of polyacrylic acid and an alcohol. Cross-linking of polyethylene or polyvinyl alcohol is more advantageous than cross-linking lower alcohols.

It is also possible to perform three dimensional cross-linking using an acid amide-forming reaction between polyacrylic acid and polyethylene amine or an acid amide exchange reaction between polyacrylamide and polyethylene amine thereby to render the polymer water-insoluble.

When a mixture of polyvinyl alcohol and another water-soluble polymer such as polyacrylic acid is reacted with an aldehyde to acetalize the polyvinyl alcohol, polyacrylic acid is entrapped in the cross-linked molecular chain. In this situation, polyacrylic acid does not participate in the cross-linking reaction.

This corresponds to the case where two or more water-soluble polymers are present together and a first of the polymers undergoes a water-solubilizing reaction, but the second of the polymers remains water-soluble and yet because of the entanglement of the second polymer by the molecular chain of the first polymer, the ability of the second polymer to freely diffuse is destroyed as if the second polymer was also subjected to a water-insolubilizing reaction.

The insolubilization treatment by ionizing radiation involves both a cross-linking reaction of the water-soluble polymer per se and a cross-linking reaction with the polytetrafluoroethylene tube. Polyvinyl alcohol in the dry state decomposes more than it cross-links when exposed to ionizing radiation, and polyvinyl alcohol, as a result, is generally called a decomposable plastic. It has been found however than in the presence of water, polyvinyl alcohol undergoes a predominantly cross-linking reaction rather than a decomposition reaction. Polyacrylamide, polyvinyl pyrrolidone, and polyacrylic acid have also been shown to cross-link. It has been confirmed that the decomposition reaction of the polytetrafluoroethylene tube is somewhat reduced by irradiating the tube while the pores of the tube are impregnated with an aqueous solution so as to exclude oxygen in the air.

Thus, even in the case of a porous polytetrafluoroethylene tube which is decomposable in the air, a gelled cross-link of the water-soluble polymer in the pores of the tube can be formed with reduced deterioration of the tube by exposing the tube to ionizing radiation at a dose of about 1 to about 6 Mrads while the pores of the tube are impregnated or coated with an aqueous solution of the water-soluble polymer. If the irradiation dose is decreased to less than about 1 Mrad, a deterioration of the polytetrafluoroethylene matrix is further reduced. However, insufficient gelling and cross-linking of the water-soluble polymer occurs, and the polymer remains partly water-soluble. Hence, the water-soluble polymer gradually dissipates, and hydrophilicity ultimately tends to be lost. At irradiation doses of greater than about 6 Mrads, the decomposition of the polytetrafluoroethylene is marked.

It has been found that, depending on whether or not water is present during the cross-linking reaction, the hydrophilicity of the cross-linked polymer, especially the water content of the polymer in the swollen state, differs greatly. In insolubilization by heat-treatment, even if water is initially present, it is entirely evaporated during heating at about 100° C., and an ultrathin film of polyvinyl alcohol is formed in the interior of and on the surface of the pores. Subsequent heat-treatment of about 150° C. to 220° C. converts this film to a water-insoluble cross-linked product. For this reason, the cross-linked polyvinyl alcohol must finally be swollen by treatment with hot water at 90° C. or more.

When the water-soluble polymer is cross-linked while it is in the form of an aqueous solution, the density of cross-linking differs according to the concentration of aqueous solution of the water-soluble polymer. Further, when the water-soluble polymer is converted to a water-insoluble crosslinked product, the product becomes a gel-like product swollen with water to the greatest possible extent. Accordingly, the swellability of the crosslinked product with water, that is, the water content of the product, varies greatly according to the method of crosslinking even when the same porous polytetrafluoroethylene tubes, the same water-soluble polymers and the same concentrations of aqueous solution are used.

Crosslinking by a chemical reaction such as acetalization, esterification or acid amide formation or by ionizing radiation takes place in the presence of water. Depending upon various factors such as the concentration of the aqueous solution of the water-soluble polymer, the concentration of the aldehyde, the dose of ionizing radiation, the temperature, and the time, a fine porous swollen gel-like product of the water-soluble polymer is impregnated in the pores of the polytetrafluoroethylene tube. It is surprising to note that the pore size of the microporous swollen gel varies from about $10\mu$ to about $0.01\mu$ or to about $0.001\mu$ by changing the above-described factors. Therefore the adsorption of plasma protein is reduced, and the inside cavity of the polytetrafluoroethylene tube can have such a smooth surface that will not disturb the streams of blood. The microporous swollen gel has a softness which scarcely hampers the entry of a fibroblast from the periphery of a vascular prosthesis.

A more preferred fibrous structure of the polytetrafluoroethylene tube of this invention can be achieved by using as one starting material a polytetrafluoroethylene tube having a microfibrous structure whose outside surface differs from the inside surface. The microporous fibrous structure comprises fibers and nodes connected to one another by the fibers. Desirably, the average fiber diameter at the outside surface of the tube is at least 2 times that at the inside surface of the tube.

Another preferred microfibrous structure is for the directions of the fibers at the inside surface of the tube to be distributed more radially than the directions of the fibers at the outer surface of the tube; or the long axes of nodes at the outside surface of the tube to be at least two times the short axes of nodes at the inside surface of the tube; or the pore size of the outside surface of the tube to be larger than the pore size of the inside surface of the tube.

In any of these microfibrous structures, the inside surface of the tube has finer diameter of the fiber and smaller pore size than the outside surface of the tube. Consequently, after implantation in the body, the rate of entry of the connective tissue from the periphery is increased, and surface stagnation of blood flowing over the inside surface of the tube is reduced. Furthermore, by filling the pores of the microfibrous structure with the water-insolubilized water-soluble polymer, platelet adhesion can be reduced.

In order to obtain such a structure, the stretched tube is sintered at about 327° C. or higher by heating the tube from the periphery of the tube while the inside surface of the tube is forcedly cooled.

The forced cooling of the inside of the tube can be achieved by continuously introducing cooled air into the inner cavity of the tube, or by continuously reducing the pressure of the inner cavity of the tube. While the inside surface of the tube is continuously exposed to cooled water in such a way, the sintering temperature of the polymeric portion on the outside surface of the tube is adjusted to about 327° C. or higher. The inside surface of the tube may, or may not, be heated to the sintering temperature. However, during the course of sintering, the temperature of the inside surface of the tube should be always lower than that of the outside surface.

As a result, the fibers at the outside surface of the tube are exposed for a long time to temperatures of about 327° C. or higher, and two or more of the fibers initially having the same fibrous structure as the inside surface (especially, with respect to fiber diameters) coalesce and become thicker. For example, in order for the fiber diameter to become two fold, four fibers are fused and coalesced.

The portion of the wall thickness of the outside surface of the tube and the wall thickness of the inside surface of the tube varies by varying the amount of the cooled air passed through the inner cavity of the tube and the amount of heat supplied externally. At this time, the sizes of the nodes do not change, and therefore, the nodular size is substantially the same both at the inside surface and the outside surface.

When the tube is stretched in the longitudinal direction and then expanded radially, that is, in the direction of the diameter of the tube, the microfibrous structure abruptly changes. When the tube is stretched only in the longitudinal direction, the nodes have an ellipsoidal shape with a relatively uniform size. When the tube is then expanded in the radial direction of the tube, the nodes formed in the longitudinal direction further separate into smaller portion depending on the degree of expansion, and fibers again occur among the nodes. The shape of the nodes, and the length, direction and diameter of the fibers vary according to the degrees of stretching in the longitudinal direction and in the radial direction. In any case, it is true that the shape, length, size, etc. of fibers change from those in the case of stretching only in the longitudinal direction, depending on the extent to which the tube is expanded in the diametrical direction after stretching in the longitudinal direction.

In a most preferred embodiment, the tube is first stretched in the longitudinal direction and then expanded in the radial direction. Before expansion in the radial direction, the outside surface of the tube is heated to a temperature above about 327° C. which is the sintering temperature of the polytetrafluoroethylene crystals, and the inside surface of the tube is maintained at a temperature of not more than about 327° C. Thus, a tube can be produced in which the outside surface of the tube is a microfibrous structure stretched only in the longitudinal direction, and the inside surface of the tube is a microfibrous structure biaxially stretched by expanding the tube also in the radial direction. Of course, it is possible to change the microfibrous structure of the outside surface and the inside surface by first expanding the tube in the radial direction and then stretching the tube in the longitudinal direction.

In accordance with the present invention and using the methods described hereinabove, the pores of these polytetrafluoroethylene tubes can be filled with a water-soluble polymer, after which the water-soluble polymer is treated to render it water-insoluble. Certain advantages are obtained, in the preferred embodiment of the invention because of the differences in the pore size and/or the diameter, strength or orientation of the fibers at the inner and outer surfaces of the tubing.

Firstly, this increases the mechanical strength of a vascular prosthesis prepared from such a polytetrafluoroethylene tube. Thus, tearing of the prosthesis in the longitudinal direction by the suture used in implant operation can be minimized or eliminated.

The function of transporting blood can be performed only by the fibrous layer at the inside surface of the tube. However, the tube should withstand a blood pressure of 120 mmHg, should not be compressed by elastic fibrous tissue which grows on the periphery of the tube, and also should be capable of withstanding joining at the time of surgery.

The tearing resistance, or the force required to break the fibers, can be increased by increasing the diameter of the fibers at the outside surface of the tube and increasing the number of fibers which run in a direction at right angles to the tearing direction. In particular, tubes which have been stretched and expanded in two directions to increase their diameters have improved tear strength.

Secondly, the fibers at the inside surface have a smaller diameter than the fibers at the outside surface, and thus the surface resistance of the prosthesis to the flow of blood can be decreased, and consequently, platelet adhesion decreases. Platelets which contact the surface of the prosthesis and adhere to the surface undergo reversible clotting with adenosine diphosphoric acid and calcium ion. Thus, the platelets from an irreversible clot, and together with fibrin, form a thrombus. The thrombus becomes a thinner layer as the amount of platelets that have adhered becomes smaller. When fibrin deposits on this initial thrombus layer, its thickness increases, and finally occlusion occurs. For this reason, to reduce the thickness of the initial thrombus layer is an essential requisite for obtaining a vascular prosthesis with which occlusion does not occur. This effect is greater in veins than in arteries. In other words, an effect of reducing the thickness of the neo-intima in the inner cavity of the vascular prosthesis can be expected.

A third effect is that with a coarse, fibrous structure of the outside surface of the vascular prosthesis, fibroblasts rapidly enter the prosthesis from periphery of the prosthesis and grow fully. It is already known that fibroblasts can easily enter a vascular prosthesis composed of a knitted or woven fabric of Dacron or polytetrafluoroethylene because the prosthesis has a wall of a coarse texture. However, immediately after implanation, bleeding occurs through the wall, and the fibrin layer in the inner cavity of the prosthesis increases. If this condition continues, the prosthesis will clot and eventually be occluded.

The benefits and advantages of the present invention can also be obtained in a polytetrafluoroethylene prosthesis having the same fibrous structure at the outside and inside surfaces, although the ease of entry of a fibroblast from the periphery of the prosthesis may be reduced.

When, as in the preferred embodiment of the present invention, the diameter of fibers at the outside surface of the prosthesis is at least two times that of the fibers at the inside surface of the prothesis, it is possible to reduce the thickness of the fibrin layer at the inside surface and simultaneously facilitate entry of the fibroblast from the periphery. Moreover, nutrient is fully supplied to the neointima formed in the inner cavity of the prosthesis through capillary vessels which grow densely on the fully grown fibroblast. It is possible to greatly reduce the phenomenon of calcification of the prosthesis due to nutritional deficiency.

Nutrient supply in vascular prostheses for arteries is performed not only be capillary vessels on the fibroblast which has entered from the periphery, but also by the blood itself in the inner cavity of the prostheses. However, in venous prostheses, nutrient supply from the blood can scarcely be expected, and nutrient supply must rely on the capillary vessels present in the fibroblast which has entered from the periphery. Hence, the entry of a fibroblast from the periphery of a vascular prosthesis is important not only for the formation of neointima, but also for preventing calcification of the prosthesis wall caused by nutritional deficiency after a lapse of time from implantation and thus increasing the patency rate of the prosthesis after operation. The importance is especially great after operation. The importance is especially great in venous prostheses.

The requirements for prostheses are that they should have a pore size small enough to prevent leakage of the circulating blood through the wall thereof and at the same time, have a large enough pore size not to hamper the entry of a fibroblast from the periphery thereof.

The vascular prostheses of this invention meet these requirements not only due to their porous characteristics such as the porosity, fiber length and pore size of the polytetrafluoroethylene tube, but also due to the condition of the water-insolubilized water-soluble polymer present in the pores of the tube.

Even a conventional vascular prosthesis made of a knitted or woven fabric of polytetrafluoroethylene which has a sufficiently large porosity, etc. to permit a leakage of the circulating blood though the wall thereof can be prevented in accordance with this invention from blood leakage through the wall thereof by filling completely the pores of the tube with a water-solubilized water-soluble polymer as a microporous swollen gel. Furthermore, a fibroblast from the periphery of the prosthesis can successively enter through the swollen gels of the water-soluble polymer, and grow.

The provision of swollen gels of a water-insolubilized water-soluble polymer in a polytetrafluoroethylene tube which has porous characteristics within the range heretofore used for vascular prostheses has the effect that the adsorption of plasma protein at the time of contact with the blood is prevented by the adsorbed water of the swollen gels or the negative charging of the swollen gels, and therefore, this inhibits the formation of a fibrin layer and consequently imparts anti-thrombosis to the vascular prosthesis.

As stated hereinabove, the vascular prosthesis of a composite structure in which the pores of a porous polytetrafluoroethylene tube are filled with a water-insolubilized water-soluble polymer gives rise to little vascular occlusion due to a thickening of a fibrin layer after a surgical operation, increases the healing speed of patients, and prevents a degeneration and retrogression of a neo-intima which have been formed. Such is not only important to surgery but also to industry.

The following Examples are given to illustrate the present invention in more detail. Unless otherwise indicated herein, all parts, percents, ratios and the like are by weight.

EXAMPLE 1

A fine Powder F-104 (Polyflon, a trademark for a product of Daikin Kogyo Kabushiki Kaisha, Japan) (3 kg) was mixed with 0.84 kg of a white oil (Sumoil P-55, a tradename for a product of Muramatsu Oil Co., Ltd., Japan). The mixture was molded into a tube with an inside diameter of 4 mm and an outside diameter of 6 mm using a ram-type extruder.

The white oil was removed from the tube by extraction with trichloroethylene. The tube, 20 cm long, was stretched to a length of 120 cm while heating the tube to 280° C. To avoid shrinkage, a stainless steel rod having an outside diameter of 3.3 mm was inserted through the stretched tube. After fixing both of the ends of the tube, the tube was placed in an oven at 355° C. After confirming that the tube had reached a temperature of 355° C., the tube was cooled, and the tube was removed from the stainless steel rod. The tube was immersed in isopropyl alcohol, and then in water.

Aqueous solutions of polyvinyl alcohol (PVA) (Kuraray Poval PVA-217, a tradename of Kuraray Co., Ltd., Japan, having an average degree of polymerization of 1750 and a degree of saponification of 88 mole%) having a concentration of 2, 4, 6, 8 and 10% by weight, respectively, were prepared. The tube immersed in water was withdrawn, and placed in each of the aqueous solutions of polyvinyl alcohol. The tube was immersed therein for at least 30 minutes, and then the excess of the adhering aqueous solution was squeezed off. The tube was sealed using a polyethylene sheet, and then exposed to an electron beam accelerator at a dose of 6 Mrads. The characteristics of the tubes obtained are shown in Table 1 below.

Table 1

| Run No. | Concentration of PVA (wt. %) | Bubble Point (kg/cm$^2$) | Inside Diameter (mm) | Wall Thickness (mm) | % Water Regain (%) |
|---|---|---|---|---|---|
| 1 | Untreated | 0.10 | 3.3 | 0.52 | 0 |
| 2 | 2 | 0.34 | 3.25 | 0.58 | 18 |
| 3 | 4 | 0.48 | 3.2 | 0.60 | 25 |
| 4 | 6 | 0.75 | 3.2 | 0.61 | 32 |
| 5 | 8 | 1.30 | 3.2 | 0.62 | 40 |
| 6 | 10 | 1.9 | 3.15 | 0.61 | 50 |

The bubble point denotes the pressure which was required to form a first bubble when the tube is immersed in isopropyl alcohol and pressure was applied from the inner cavity of the tube. The bubble point was determined using the method of ASTM F316-70. The bubble point is related to the maximum pore size of a porous body, and with a smaller maximum pore size, the bubble point becomes higher. Thus, the maximum pore size of the vascular prosthesis is smaller when the concentration of polyvinyl alcohol is higher, and therefore, the tube has a smoother surface as a vascular prosthesis.

The % water regain is the percentage of the weight increase which the tube gained when the tube was heated at 150° C. for 30 minutes to evaporate water completely therefrom and the tube was again immersed into water at 20° C., based on the weight of the tube after drying. The water content is related to the amount of water molecules strongly bonded to the polyvinyl alcohol, and therefore is correlated with the amount of plasma protein adsorbed.

EXAMPLE 2

The same mixture as described in Example 1 was extruded into a tube having an inside diameter of 3 mm and an outside diameter of 4.5 mm. The white oil was removed from the tube by extraction with trichloroethylene. The tube was then fed at a speed of 17.5 cm/min. into an electric furnace (length 35 cm) heated at 360° C. and opened at the front and rear ends, and wound up at a speed of 52.5 cm/min. As a result the tube was stretched to three times its original length.

Then, the stretched tube was fed at a speed of 70 cm/min. into an electric furnace (length 40 cm) heated at 500° C. At the outlet of the electric furnace was fitted a device (15 cm in length) whereby the pressure around the periphery of the tube was reduced. By reducing the pressure to about 10 to 20 torr using this device, the inside diameter of the tube increased from 3 mm to 4.3 mm.

When the resulting tube was immersed in isopropyl alcohol and pressure was applied through the internal cavity of the tube, the tube had a bubble point of 0.31 kg/cm$^2$. When the tube was turned inside out, the tube had a bubble point of 0.25 kg/cm$^2$. This means that the maximum pore sizes of the outside and inside surfaces are different.

Mixed aqueous solutions of polyvinyl alcohol (Kuraray Poval PVA-217 as described in Example 1) and polyacrylic acid (molecular weight about 200,000) in the concentrations shown in Table 2 below were prepared. Each of the solutions was forced into the inner cavity of the tube under a pressure of 3 kg/cm$^2$. The mixed aqueous solution exuded from the entire surface of the tube. After washing, the excess of the mixed aqueous solution on the outside surface of the tube was wiped off. The tube was then immersed for 2 minutes in a glyoxal bath, then heated at 100° C. for 20 seconds, and washed with water. The glyoxal bath used was prepared by adding 2 parts by weight of sulfuric acid and 0.5 part by weight of sodium sulfate to an aqueous solution of glyoxal having a concentration of about 40% by weight.

The tubes obtained had the characteristics shown in Table 2 below.

Table 2

| Run No. | Concentration (%) PVA | Concentration (%) PAA* | Bubble Point (kg/cm$^2$) | Inside Diameter (mm) | Wall Thickness (mm) | Tear Strength (g/ply) |
|---|---|---|---|---|---|---|
| 7 | 0 | 0 | 0.31 | 4.3 | 0.42 | 165 |
| 8 | 1.5 | 5 | 0.75 | 4.1 | 0.44 | 320 |
| 9 | 3 | 5 | 0.70 | 4.0 | 0.44 | 400 |
| 10 | 5 | 5 | 0.65 | 3.9 | 0.45 | 570 |
| 11 | 1.0 | 3.3 | 0.39 | 4.1 | 0.43 | 520 |
| 12 | 3 | 0 | 0.32 | 3.9 | 0.43 | 300 |
| 13 | 6 | 0 | 0.47 | 3.9 | 0.44 | 580 |
| 14 | 0 | 3 | 0.24 | 4.2 | 0.42 | 180 |
| 15 | 0 | 6 | 0.24 | 4.2 | 0.42 | 210 |

*PAA: polyacrylic acid

When the concentration of the aqueous solution increased, the bubble point of the tube tended to increase, and the inside diameter of the tube somewhat decreased.

The tear strength of the tube wall is a property of a vascular prosthesis in a joining operation using a suture. It is seen from the above results that the tubes in accordance with this invention have a far higher tear strength than a tube not treated with the aqueous solution of the water-soluble polymers.

It was confirmed that the tubes treated with an aqueous solution of polyacrylic acid exhibited a neutralization reaction in an aqueous solution of potassium hydroxide, and the dissociated carboxyl groups were negatively charged.

EXAMPLE 3

An aqueous solution of polyacrylic acid in a concentration of 3 and 6% by weight respectively was forced into the same type of tube as described in Example 2. Each of the tubes was immersed for 1 minute in an ethylene glycol bath (containing 10% by weight of sulfuric acid), heated for 20 seconds in a heating oven at 100° C., and then washed with water.

The resulting tubes had a bubble point of 0.32 kg/cm$^2$ (at a concentration of 3%), and 0.40 kg/cm$^2$ (at a concentration of 6%), and a tear strength of 200 g/ply (at a concentration of 3%) and 230 g/ply (at a concentration of 6%).

EXAMPLE 4

The same procedure as in Example 1 was performed except that an 8% aqueous solution of polyvinyl pyrrolidone was used instead of the polyvinyl alcohol solution. The tube obtained had a bubble point of 1.4 kg/cm$^2$, whereas a tube not treated with the polyvinyl pyrrolidone solution had a bubble point of 0.1 kg/cm$^2$.

EXAMPLE 5

A 4% aqueous solution of polyvinyl alcohol (Kuraray Poval PVA-217 as described in Example 1) was forced into the same type of tube as described in Example 2. The tube was heated for 10 minutes in a heating oven at 180° C., and treated for 10 minutes with hot water at 90° C. The tube had a water content of 38%.

When the tube was treated with a mixed aqueous solution containing 3% of polyethylene glycol and 6% of the polyvinyl alcohol, and heat-treated under the same conditions, the resulting tube had a water content of 120%.

While the invention has been described in detail and with reference to specific embodiments thereof, it will be apparent to one skilled in the art that various changes and modifications can be made therein without departing from the spirit and scope thereof.

What is claimed is:

1. A composite structure vascular prosthesis comprising a porous polytetrafluoroethylene tube in which the pores of the porous polytetrafluoroethylene tube are filled with at least one water-insolubilized water-soluble polymer.

2. The vascular prosthesis of claim 1, wherein the water-insolubilized water-soluble polymer is partly or completely crosslinked to form a microporous swollen gel.

3. The vascular prosthesis of claim 2, wherein the porous polytetrafluoroethylene tube has a microstructure of nodes connected to one another by fibers, and the microstructure differs between the outside surface of the porous polytetrafluoroethylene tube and the inside surface of the porous polytetrafluoroethylene tube.

4. The vascular prosthesis of claim 2, wherein the water-soluble polymer is a polymer containing a hydroxyl group.

5. The vascular prosthesis of claim 4, wherein the hydroxyl group-containing polymer is polyvinyl alcohol.

6. The vascular prosthesis of claim 2, wherein the water-soluble polymer is a polymer containing a carboxyl group.

7. The vascular prosthesis of claim 6, wherein the carboxyl group-containing polymer is polyacrylic acid.

8. The vascular prosthesis of claim 2, wherein the water-soluble polymer is a polymer containing nitrogen.

9. The vascular prosthesis of claim 8, wherein the nitrogen containing-polymer is polyvinyl pyrrolidone.

10. The vascular prosthesis of claim 2, wherein the water-soluble polymer is a mixture of a carboxyl group-containing polymer and a hydroxyl group-containing polymer.

11. The vascular prosthesis of claim 10, wherein the water-soluble polymer is a mixture of polyacrylic acid and polyvinyl alcohol.

12. The vascular prosthesis of claim 2, wherein the water-soluble polymer is a mixture of a nitrogen-containing polymer and a hydroxyl group-containing polymer.

13. The vascular prosthesis of claim 12, wherein the water-soluble polymer is a mixture of polyvinyl alcohol and polyvinyl pyrrolidone.

14. The vascular prosthesis of claim 1, wherein the porous polytetrafluoroethylene tube has a microstructure of nodes connected to one another by fibers, and the microstructure differs between the outside surface of the porous polytetrafluoroethylene tube and the inside surface of the porous polytetrafluoroethylene tube.

15. The vascular prosthesis of claim 14, wherein the diameter of fibers at the outside surface of the porous polytetrafluoroethylene tube is at least two times the diameter of the fibers at the inside surface of the porous polytetrafluoroethylene tube.

16. The vascular prosthesis of claim 14, wherein the directions of the fibers at the inside surface of the porous polytetrafluoroethylene tube are distributed more radially than those of the fibers at the outside surface of the porous polytetrafluoroethylene tube.

17. The vascular prosthesis of claim 14, wherein the long axis of each node at the outside surface of the porous polytetrafluoroethylene tube is at least two times the long axis of each node at the inside surface of the porous polytetrafluoroethylene tube.

18. The vascular prosthesis of claim 14, wherein the pore size of the outside surface of the porous polytetrafluoroethylene tube is larger than the pore size of the inside surface of the porous polytetrafluoroethylene tube.

19. The vascular prosthesis of claim 1, wherein the water-soluble polymer is a polymer containing a hydroxyl group.

20. The vascular prosthesis of claim 19, wherein the hydroxyl group-containing polymer is polyvinyl alcohol.

21. The vascular prosthesis of claim 1, wherein the water-soluble polymer is a polymer containing a carboxyl group.

22. The vascular prosthesis of claim 21, wherein the carboxyl group-containing polymer is polyacrylic acid.

23. The vascular prosthesis of claim 1, wherein the water-soluble polymer is a polymer containing nitrogen.

24. The vascular prosthesis of claim 23, wherein the nitrogen-containing polymer is polyvinyl pyrrolidone.

25. The vascular prosthesis of claim 1, wherein the water-soluble polymer is a mixture of a carboxyl group-containing polymer and a hydroxyl group-containing polymer.

26. The vascular prosthesis of claim 25, wherein the water-soluble polymer is a mixture of polyacrylic acid and polyvinyl alcohol.

27. The vascular prosthesis of claim 1, wherein the water-soluble polymer is a mixture of a nitrogen-containing polymer and a hydroxyl group-containing polymer.

28. The vascular prosthesis of claim 27, wherein the water-soluble polymer is a mixture of polyvinyl alcohol and polyvinyl pyrrolidone.

* * * * *

UNITED STATES PATENT AND TRADEMARK OFFICE
CERTIFICATE OF CORRECTION

PATENT NO. : 4,193,138
DATED : March 18, 1980
INVENTOR(S) : Koichi Okita

It is certified that error appears in the above—identified patent and that said Letters Patent is hereby corrected as shown below:

The attached columns 11 & 12 should be inserted immediately following columns 9 & 10.

THIS CERTIFICATE OF CORRECTION APPLYS TO THE GRANT EXCLUSIVELY.

Signed and Sealed this

Tenth Day of June 1980

[SEAL]

Attest:

SIDNEY A. DIAMOND

Attesting Officer    Commissioner of Patents and Trademarks entry of a fibroblast from the periphery of a vascular prosthesis is important not only for the formation of neointima, but also for preventing calcification of the prosthesis wall caused by nutritional deficiency after a lapse of time from implantation and thus increasing the patency rate of the prosthesis after operation. The importance is especially great after operation. The importance is especially great in venous prostheses.

The requirements for prostheses are that they should have a pore size small enough to prevent leakage of the circulating blood through the wall thereof and at the same time, have a large enough pore size not to hamper the entry of a fibroblast from the periphery thereof.

The vascular prostheses of this invention meet these requirements not only due to their porous characteristics such as the porosity, fiber length and pore size of the polytetrafluoroethylene tube, but also due to the condition of the water-insolubilized water-soluble polymer present in the pores of the tube.

Even a conventional vascular prosthesis made of a knitted or woven fabric of polytetrafluoroethylene which has a sufficiently large porosity, etc. to permit a leakage of the circulating blood though the wall thereof can be prevented in accordance with this invention from blood leakage through the wall thereof by filling completely the pores of the tube with a water-solubilized water-soluble polymer as a microporous swollen gel. Furthermore, a fibroblast from the periphery of the prosthesis can successively enter through the swollen gels of the water-soluble polymer, and grow.

The provision of swollen gels of a water-insolubilized water-soluble polymer in a polytetrafluoroethylene tube which has porous characteristics within the range heretofore used for vascular prostheses has the effect that the adsorption of plasma protein at the time of contact with the blood is prevented by the adsorbed water of the swollen gels or the negative charging of the swollen gels, and therefore, this inhibits the formation of a fibrin layer and consequently imparts antithrombosis to the vascular prosthesis.

As stated hereinabove, the vascular prosthesis of a composite structure in which the pores of a porous polytetrafluoroethylene tube are filled with a water-insolubilized water-soluble polymer gives rise to little vascular occlusion due to a thickening of a fibrin layer after a surgical operation, increases the healing speed of patients, and prevents a degeneration and retrogression of a neo-intima which have been formed. Such is not only important to surgery but also to industry.

The following Examples are given to illustrate the present invention in more detail. Unless otherwise indicated herein, all parts, percents, ratios and the like are by weight.

EXAMPLE 1

A fine Powder F-104 (Polyflon, a trademark for a product of Daikin Kogyo Kabushiki Kaisha, Japan) (3 kg) was mixed with 0.84 kg of a white oil (Sumoil P-55, a tradename for a product of Muramatsu Oil Co., Ltd., Japan). The mixture was molded into a tube with an inside diameter of 4 mm and an outside diameter of 6 mm using a ram-type extruder.

The white oil was removed from the tube by extraction with trichloroethylene. The tube, 20 cm long, was stretched to a length of 120 cm while heating the tube to 280° C. To avoid shrinkage, a stainless steel rod having an outside diameter of 3.3 mm was inserted through the stretched tube. After fixing both of the ends of the tube, the tube was placed in an oven at 355° C. After confirming that the tube had reached a temperature of 355° C., the tube was cooled, and the tube was removed from the stainless steel rod. The tube was immersed in isopropyl alcohol, and then in water.

Aqueous solutions of polyvinyl alcohol (PVA) (Kuraray Poval PVA-217, a tradename of Kuraray Co., Ltd., Japan, having an average degree of polymerization of 1750 and a degree of saponification of 88 mole%) having a concentration of 2, 4, 6, 8 and 10% by weight, respectively, were prepared. The tube immersed in water was withdrawn, and placed in each of the aqueous solutions of polyvinyl alcohol. The tube was immersed therein for at least 30 minutes, and then the excess of the adhering aqueous solution was squeezed off. The tube was sealed using a polyethylene sheet, and then exposed to an electron beam accelerator at a dose of 6 Mrads. The characteristics of the tubes obtained are shown in Table 1 below.

Table 1

| Run No. | Concentration of PVA (wt. %) | Bubble Point (kg/cm$^2$) | Inside Diameter (mm) | Wall Thickness (mm) | % Water Regain (%) |
|---|---|---|---|---|---|
| 1 | Untreated | 0.10 | 3.3 | 0.52 | 0 |
| 2 | 2 | 0.34 | 3.25 | 0.58 | 18 |
| 3 | 4 | 0.48 | 3.2 | 0.60 | 25 |
| 4 | 6 | 0.75 | 3.2 | 0.61 | 32 |
| 5 | 8 | 1.30 | 3.2 | 0.62 | 40 |
| 6 | 10 | 1.9 | 3.15 | 0.61 | 50 |

The bubble point denotes the pressure which was required to form a first bubble when the tube is immersed in isopropyl alcohol and pressure was applied from the inner cavity of the tube. The bubble point was determined using the method of ASTM F316-70. The bubble point is related to the maximum pore size of a porous body, and with a smaller maximum pore size, the bubble point becomes higher. Thus, the maximum pore size of the vascular prosthesis is smaller when the concentration of polyvinyl alcohol is higher, and therefore, the tube has a smoother surface as a vascular prosthesis.

The % water regain is the percentage of the weight increase which the tube gained when the tube was heated at 150° C. for 30 minutes to evaporate water completely therefrom and the tube was again immersed into water at 20° C., based on the weight of the tube after drying. The water content is related to the amount of water molecules strongly bonded to the polyvinyl alcohol, and therefore is correlated with the amount of plasma protein adsorbed.

EXAMPLE 2

The same mixture as described in Example 1 was extruded into a tube having an inside diameter of 3 mm and an outside diameter of 4.5 mm. The white oil was removed from the tube by extraction with trichloroethylene. The tube was then fed at a speed of 17.5 cm/min. into an electric furnace (length 35 cm) heated at 360° C. and opened at the front and rear ends, and wound up at a speed of 52.5 cm/min. As a result the tube was stretched to three times its original length.

Then, the stretched tube was fed at a speed of 70 cm/min. into an electric furnace (length 40 cm) heated at 500° C. At the outlet of the electric furnace was fitted a device (15 cm in length) whereby the pressure around the periphery of the tube was reduced. By reducing the pressure to about 10 to 20 torr using this device, the